(12) United States Patent
O'Brien et al.

(10) Patent No.: US 7,370,537 B2
(45) Date of Patent: May 13, 2008

(54) CERAMIC BALL BEARING ACOUSTIC TEST METHOD

(75) Inventors: Michael J. O'Brien, Los Angeles, CA (US); Benjamin A. Nelson, Los Angeles, CA (US); Michael R. Hilton, Westminster, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 10/989,180

(22) Filed: Nov. 15, 2004

(65) Prior Publication Data

US 2006/0101913 A1    May 18, 2006

(51) Int. Cl.
*G01N 3/08* (2006.01)
*G01N 29/00* (2006.01)

(52) U.S. Cl. .............................. 73/818; 73/587; 73/600

(58) Field of Classification Search .................. 73/587, 73/593, 599, 600, 602, 584, 660, 629, 818–825; 384/448, 492
See application file for complete search history.

(56) References Cited

U.S. PATENT DOCUMENTS

| 5,257,544 | A  | * | 11/1993 | Khuri-Yakub et al. | ........ 73/579 |
| 5,355,731 | A  | * | 10/1994 | Dixon et al. | ................... 73/579 |
| 5,398,551 | A  | * | 3/1995  | Kawasaki et al. | ............ 73/593 |
| 5,493,511 | A  | * | 2/1996  | Wincheski et al. | ........... 702/39 |
| 5,714,687 | A  | * | 2/1998  | Dunegan | ...................... 73/587 |
| 6,173,613 | B1 | * | 1/2001  | Dunegan | ...................... 73/587 |
| 6,360,608 | B1 | * | 3/2002  | Dunegan | ...................... 73/587 |
| 6,725,720 | B2 | * | 4/2004  | Kiuchi et al. | .................. 73/593 |
| 6,952,969 | B2 | * | 10/2005 | O'Brien et al. | ............... 73/818 |
| 2002/0121141 | A1 | * | 9/2002  | Kiuchi et al. | .................. 73/587 |
| 2003/0183021 | A1 | * | 10/2003 | Holmberg | .................. 73/865.3 |
| 2006/0048576 | A1 | * | 3/2006  | Kiuchi et al. | .................. 73/593 |

\* cited by examiner

*Primary Examiner*—Hezron Williams
*Assistant Examiner*—Jacques M. Saint-Surin
(74) *Attorney, Agent, or Firm*—Derrick Michael Reid

(57) ABSTRACT

An acoustical mechanical test method prescribes compressing brittle balls in spherical conforming opposing platens producing equatorial bulging, tensile stresses, and resulting in crack or flaw growth with emissions of acoustical sounds for direct identification of brittle balls having a flaw exceeding a maximum allowable size, such as flaws in silicon-nitride balls used in hybrid bearings as well as conventional steel ball bearings.

12 Claims, 5 Drawing Sheets

FRACTURE SOUND PROOF TEST FIXTURE

FRACTURE SOUND PROOF TEST FIXTURE

ACOUSTIC FLAW IDENTICATION MEASUREMENT PROCESS

COMPRESSIVE STRESS CONTOUR PLOT

TENSILE STRESS CONTOUR PLOT

LONGITUDINAL DISTANCE AND STRESS GRAPH

CERAMIC BALL BEARING ACOUSTIC TEST METHOD

STATEMENT OF GOVERNMENT INTEREST

The invention was made with Government support under contract No. F04701-00-C-0009 by the Department of the Air Force. The Government has certain rights in the invention.

FIELD OF THE INVENTION

The invention relates to the field of materials proof testing. More particularly, the present invention relates to ceramic and metallic ball bearing proof testing for manufacturing and qualifying high quality brittle ball bearings.

BACKGROUND OF THE INVENTION

Over the last decade, silicon-nitride $Si_3N_4$ balls have become an important component of advanced bearings used in a wide range of applications. The greatest commercial success for $Si_3N_4$ balls has been their use in hybrid bearings that combine the ceramic balls with steel races and that are known as silicon-nitride hybrid bearings. Compared to the steel balls, which the silicon-nitride balls replace, the ceramic balls are harder and less dense and offer higher compressive strength, better corrosion resistance, elevated operating temperature, and reduced lubrication requirements. These benefits make the hybrid bearings ideal for severe high-speed applications such as machine tool spindles, high-speed dental drills, vacuum turbomolecular pumps, and the liquid-oxygen turbomolecular pumps used in the space shuttle main engines. Large diameter ceramic balls recently became the leading technology for hip replacements.

For exemplar future use in the space industry, the hybrid bearings have been proposed for the improved momentum control wheels and flywheels for satellites. Importantly, the hybrid bearings have recently been used in roller blades, an application where the bearings represent a mass marketing opportunity for lightweight rugged bearings. The roller blade market, as well as other commercial applications, provides recreational users and athletes with cost-effective high technology long-lasting bearings with improved performance in high volumes that would lower the price of the hybrid bearings for all applications with increasing overall sales. For machine tool spindles, the market for hybrid bearings was at $35 million in 2000 and is projected to reach $150 million by 2005, and hence there is wide spread usage. The overall sales of hybrid bearings should reach several hundred million by 2010. Hence, there is a significant need for high-volume hybrid bearings subject to repeatable and accurate manufacturing requirements.

Ceramic balls have significant drawbacks and limitations. Like all ceramics, the silicon-nitride balls have a low tensile strength, which is a fundamental material property. Therefore, under applied tension, the balls are prone to crack either at a preexisting manufacturing flaw or at a flaw that develops during service and usage. A closely related fundamental material property is the fracture toughness, which indicates the susceptibility to fracture of the ceramic material. Low fracture toughness is the most important factor determining the ruggedness and usefulness of all ceramics in general as well as the silicon-nitride balls, in particular. Fortunately, highly engineered ceramics have been developed whose fracture toughness can be significantly increased through processing that controls microstructures. Precise manufacturing can control the size and number of preexisting flaws. To produce tougher ceramics is therefore a two-fold task. First, a microstructure is selected that is intrinsically tougher, which reduces the severity of any flaws. Second, the preexisting flaws are eliminated, which ameliorates the low fracture toughness.

In the specific case of silicon-nitride balls, manufacturing processing has been developed that provides, for example, a two-phase microstructure of alpha and beta silicon nitride where the minor second phase is a blocky shape in a matrix of the major phase. As a micromechanism, this microstructure promotes crack deflection and blunting, which raises the intrinsic fracture toughness. In addition, the ceramic balls are manufactured from a starting powder through hot-isostatic pressing that is followed by grinding and lapping to provide precise spherical shapes. Accurate control of the hot-isostatic pressing eliminates sintering voids and inclusions that are potential preexisting flaws leading to potential fracture and failure of the balls. Precise control of the grinding and lapping eliminates surface cracks. Inspection and nondestructive evaluations are also used to screen balls with preexisting flaws from usage especially in critical applications.

Another disadvantage for any brittle material is that any preexisting cracks are atomically sharp. Only a ductile material offers the crack tip blunting needed for a crack to depart from atomic sharpness. In the unloaded state, the opposite faces of an atomically sharp crack are close together and mate almost perfectly with a negligibly perceptible gap between the two faces.

Physically, the negligible gap minimizes the contrast of the crack exploited by conventional inspection methods. Hence, to conventional inspection methods, the atomically sharp crack appears to be healed and appears to be virgin uncracked material. That is, current inspection methods find it difficult to differentiate between cracked and uncracked material in a ceramic. The limit of resolution of current inspection methods is therefore raised when applied to a ceramic, and the smallest identifiable flaw is unfortunately quite high. Of course, the goal of any inspection method is to identify as small a flaw as possible.

The leading inspection technique used by the ball manufacturers is florescent penetrant dye. In this method, the ball is placed in a bath of liquid florescent dye. Any preexisting crack looks like a free surface to the liquid and therefore has a tendency to wick the dye into itself due to surface energy effects. The crack therefore is a potential reservoir for the dye. The ball is removed from the bath, wiped clean and viewed under black light. The preexisting crack will continuously ooze fluid, which will be visible under black light. The method relies upon the human eye to detect the contrast between florescent and unflorescent regions.

The florescent dye technique has physical limits on the smallest crack that can be resolved and detected. One natural limit is the acuity of human vision. Another limit for brittle ceramics is that an atomically sharp crack represents a very small reservoir and therefore a very low driving force to wick dye. Fundamentally, therefore, an atomically sharp crack provides very low contrast. For the florescent dye technique, the limit of resolution of crack depth exceeds 0.1 mm under ideal laboratory conditions. The limit probably exceeds 0.2 mm under practical factory conditions that must depend upon the attentiveness of an operator who becomes fatigued after many hours of inspection.

Other possible techniques rely upon reflective radiation, such as ultrasound, or transmissive radiation, such as x-ray.

In the case of ultrasound, the preexisting flaw reflects an anomalous sound wave that is not reflected by the uncracked material. Physically, the reflection from the crack is the source of contrast that must be detected. Unfortunately, an atomically sharp flaw in a ceramic reflects a very small echo because the flaw appears to be almost perfectly closed. Only a relatively deep crack, on the order of 1.0 mm, becomes visible under the ultrasound method.

X-ray techniques rely upon differential absorption across the flaw, which is again very low for an atomically sharp flaw that appears to the X-ray to be closed. Another limitation is the sensitivity of the film or X-ray detector used to measure the differential absorption. The limit of resolution of a crack probably exceeds 1.0 mm for the X-ray method. As additional drawbacks, the ultrasound and X-ray techniques both require a well-trained operator and very expensive equipment. For these reasons, the X-ray and ultrasound techniques are currently not used by the ball manufacturers.

The hallmark of all current inspection methods is that a detector is used to identify a source of contrast possessed by a crack that is not possessed by uncracked material. A new replacement method is obviously needed to overcome the shortcomings of the current state-of-the-art inspection method, so that cracks much smaller than 0.1 mm can be reliably detected. If the new method can qualify the balls as defect-free to this finer limit of resolution, then the balls can be reliably used in new safety-critical applications such as turbine engines. A better inspection method offers two related benefits. First, the predicted lifetime of the ball becomes much longer. Second, the confidence in the lifetime is much greater.

The industrial inspection methods currently used have great difficulty resolving preexisting flaws that are atomically sharp because these flaws appear to be almost perfectly closed under the current methods. Disadvantageously, there is no current known test that can independently measure the fracture toughness of the ceramic balls. The existing inspection methods are disadvantageously not well suited to find cracks in brittle materials that are atomically sharp. Disadvantageously, the existing leading test method, florescent penetrant dye, can only detect surface cracks open to the environment and can not detect subsurface flaws, which are an important class of flaws leading to premature failure in service. All of the current industrial practices are disadvantageously highly labor intensive and rely upon the attentiveness and acuity of a human operator. These and other disadvantages are solved or reduced using the invention.

SUMMARY OF THE INVENTION

An object of the invention is to provide a flaw identification test method for brittle balls.

Another object of the invention is to provide an acoustic flaw identification test method for brittle balls.

Yet another object of the invention is to provide an acoustic flaw identification test method for brittle balls using applied compressive loads to produce tensile stress.

Still another object of the invention is to provide an acoustic flaw identification test method for brittle balls using applied compressive loads to produce tensile stress while directly observing acoustical crack growth sounds.

A further object of the invention is to provide an acoustic flaw identification test method for brittle balls using compressive conforming north-south opposing arc loads while directly observing acoustical crack growth sounds.

The present invention is directed to a mechanical test method for directly identifying flaws in brittle balls such as ceramic and steel ball bearings. For example, the mechanical test method can be used to directly identify flaws of the silicon-nitride balls used in hybrid bearings. Using this acoustical test method, a ball is placed between opposing platens that have hemispherical sockets with radii equal and conforming to the radius of the spherical ball under test. Importantly, the depth of the hemispherical sockets is less than the radius of the ball, such that the sockets are not a complete hemisphere and such that the angular arc length of the socket from the mating north and south poles of the sockets is less than ninety degrees. Consequently, the middle span of the ball, particularly about the equator of the ball, is not in contact with the hemispherical shaped sockets.

Preferably, two opposing platens are pushed towards each other under an applied load along the vertical axis through the respective opposing north and south poles of the two opposing platens. Under the applied load, as the inner socket surfaces apply compression forces upon the ball under test along the conforming angular arc length, the middle span of the ball at the equator slightly bulges outwardly. This equatorial bulging causes a tensile stress in the angular or hoop direction at the middle span along the equator of the brittle ball under test. Under a sufficiently high-applied load, a tensile hoop stress develops at the middle span that is intense enough to cause a crack or flaw to grow in length while producing noise. The flaw growth noise is preferably directly observed by an acoustical microphone. As part of the direct acoustic test method, the ball under test emits sounds from a flaw when the ball is compressed. The acoustical test method is specialized for the spherical brittle balls that may have small spherical volumes.

The acoustic test method directly identifies the largest preexisting flaw present in actual silicon-nitride balls upon testing. The acoustic test method overcomes the shortcomings of the methods currently used to measure the largest flaws present in the balls. The acoustic test offers an economical approach to identify small flaws, making the test method of great practical utility. The acoustic test method is well suited to identify and resolve atomically sharp flaws.

The acoustic test method can be applied to mass-produced silicon-nitride balls for the presence of preexisting flaws. The acoustic test method is robust and cost-effective enough to be used for quality control by manufacturers and for qualification by contractors installing the balls in critical applications. As an added benefit, a robust quality control manufacturing screening test offers the ability to specify the maximum allowable flaw size, as a purchasing requirement. The manufacturing screening proof test can also be incorporated into statistical process control on a manufacturing factory floor to reduce cost, improve quality, and to evaluate independently the success of the inspection and nondestructive evaluations. In addition, the manufacturing screening proof test can be used to research how changes in materials processing control the population of preexisting flaws so as to provide testing feedback between various manufacturing processes and the quality of the ceramics. These and other advantages will become more apparent from the following detailed description of the preferred embodiment.

DETAILED DESCRIPTION OF THE PREFERRED EMBODIMENT

Figure 1:
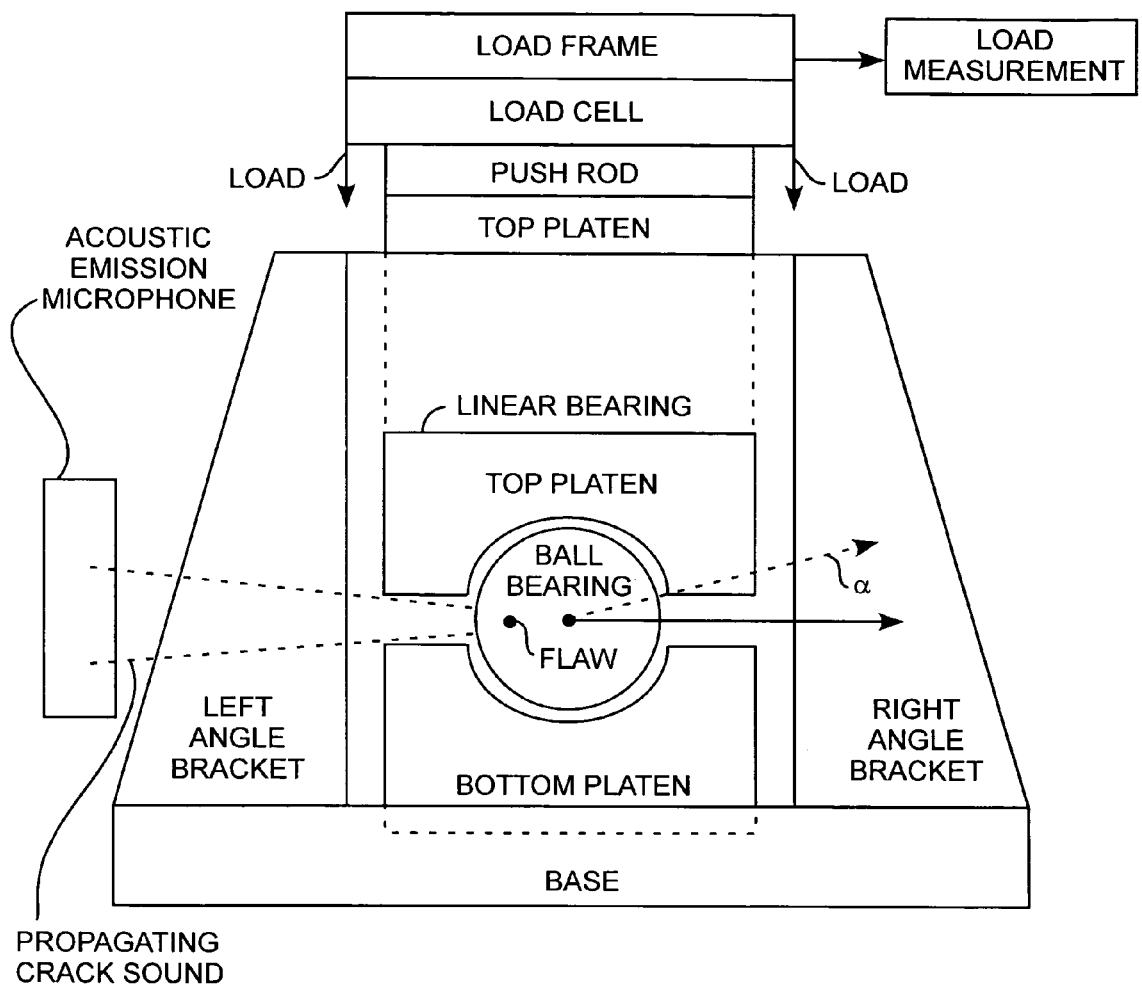
FIG. 1 is a diagram of a soundproof test fixture.

An embodiment of the invention is described with reference to the figures using reference designations as shown in the figures. Referring to FIG. 1, the mechanical test method can be implemented using a proof test fixture for directly identifying preexisting flaws and preexisting cracks in ceramic balls, such as are used in modern hybrid bearings. In practicing the method, the ball is placed between opposing platens that have hemispherical sockets with radii equal to the radius of the ball radius. However, the depth of the hemispherical sockets is less than the radius of the ball. That is, the sockets of the platens have a radial arc length that is less than a complete hemisphere such that the conforming arc length is less than ninety degrees from the north pole for the top platen and equally less than ninety degrees for the south pole, so that the midspan or equator of the ball does not contact the incompletely conforming hemispherical sockets because the depth of the sockets is less than the radius of the ball. The depth of the sockets is defined by the conforming angle $\alpha$. Hence, the incompletely conforming hemisphere sockets are defined by the conforming angle $\alpha$ that is less than ninety degree from the poles, and, in the preferred form, is 75±10 degree. The nominal 75° off the poles of the platens is an optimum conforming angle $\alpha$ that is also nominally 15° off the equator of the ball.

To run the test, the two platens are compressed along the vertical axis extending through the north and south poles of the two platens as well as the ball under test. Using this vertically aligned pole orientation, the ball is compressed by the platens at the north pole and south pole. The middle span at the equator of the ball is not in contact with the incompletely conforming hemispherical sockets. A load cell is used for providing a measurement of the applied load. The load frame uses a push rod to apply the load to the top platen towards the bottom platen supporting the ball under test. The top platen is supported by and moves through a linear bearing. The load frame may be an adapted Instron load frame. The ball rests in the conforming socket of the bottom platen. The linear bearing is disposed between left and right frame brackets coupled and supported by a base in which is disposed the bottom platen. Under a nominal applied load, the push rod pushes the top platen through the linear bearing towards the bottom platen until the conforming socket of the top platen makes contact with the ball under test with the north poles and south poles of the top and bottom sockets aligned with the north and south poles of the ball under test. At the time of contact, the applied load increases so as to apply a compressive force upon the ball across the conforming sockets. The middle equator of the ball begins to bulge outwardly as the applied load is increased, causing a tensile stress in a hoop direction at the equator. The preexisting crack begins to grow under the tensile stress. A monitoring device, such as a microphone or an acoustic emissions transducer, can be used to monitor the crack growth while the ball is under the applied load, such that the test fixture can provide evidence of crack growth under the applied load, from which the crack size can be automatically computed by a computer that receives the acoustic signal from the microphone and applied load data from the load cell. If no crack growth is detected, then an upper bound can be placed on the largest possible flaw size that can be present in the ball. The microphone can be adapted to include or couple to a computer processor receiving applied load data from the load cell while further receiving crack growth acoustic signals from the microphone. The microphone can be coupled to the ball in various ways, including gluing the microphone to the test fixture or by placing the microphone in a small tub of oil in which the test ball sits. The microphone signal is amplified and registers a peak voltage when the crack grows. The peak voltage can be a fraction of a volt above ambient background noise.

Figure 2:
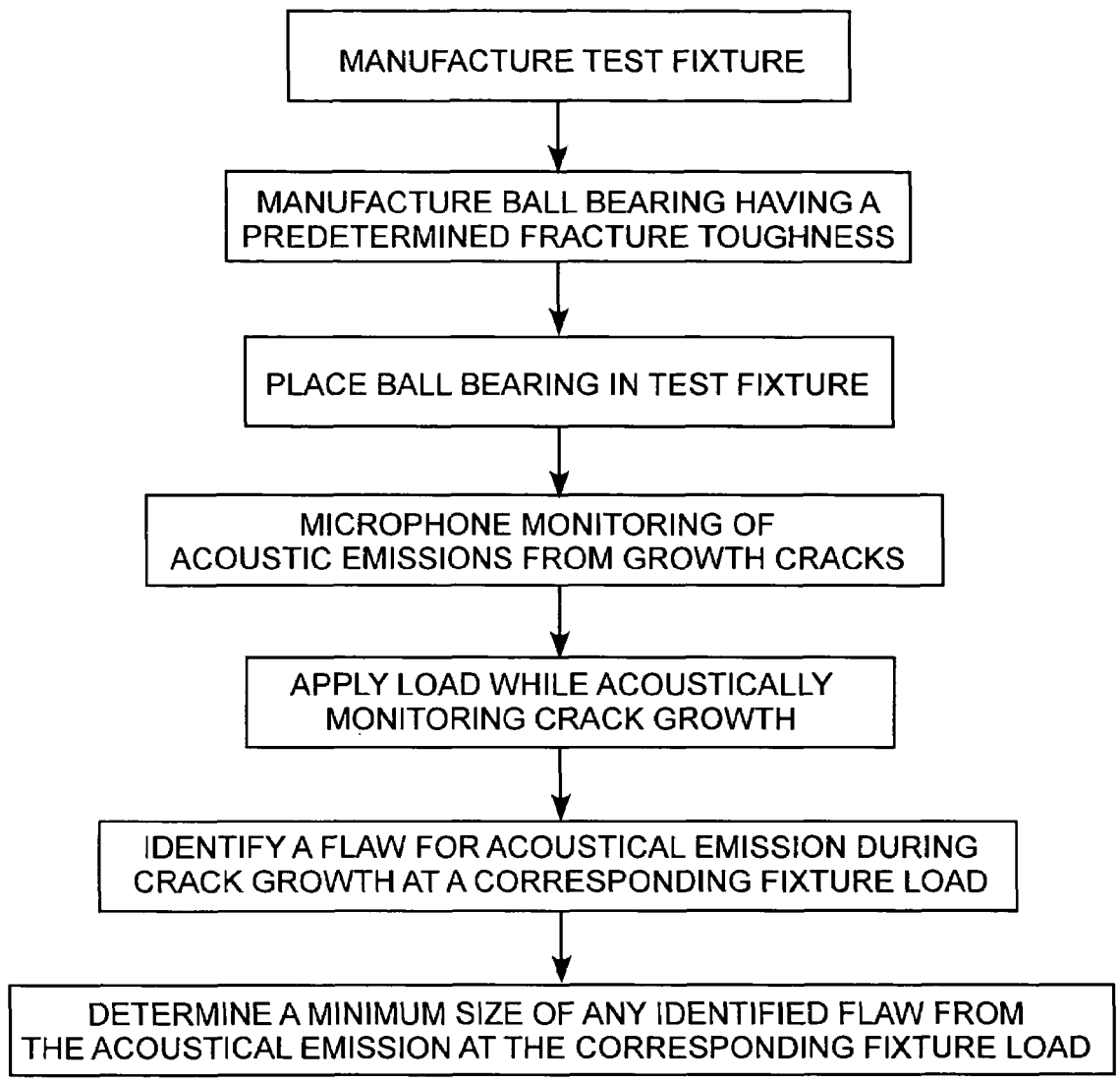
FIG. 2 is a flow diagram of an acoustic flaw identification measurement process.

Referring to FIGS. 1 and 2, and more particularly FIG. 2, the test method is preferably implemented using a manufactured test fixture, such as the preferred acoustic flaw identification test fixture shown in FIG. 1. A brittle ball is manufactured. The brittle ball can be made of various materials, such as from ceramics and steel. The ball is positioned in the bottom platen. The load frame applies an initial low push load to the push rod to push the top platen towards the ball until the conforming socket of the top platen makes conforming mating contact with the north hemispherical surface of the ball under test. The load frame then applies an increasing amount of load upon the top platen to apply an increasing amount of load upon the ball. Under a sufficiently high-applied load, a tensile hoop stress develops at the equator that is intense enough to cause any preexisting crack or flaw of a predetermined size to grow, generating acoustical emissions that are monitored by a microphone. In practice, the ball is turned several times and retested so that the entire ball is exposed to the tensile stress. The crack growth is observed directly by microphone detection of acoustic emissions radiated by the growing crack. Using computational processes, an estimate of the minimum flaw size is defined by the observed load at which the flaw grows while emitting acoustical emissions and the fracture toughness of the material, which is measured independently a priori. If no crack growth is detected by an absence of acoustical emissions, an upper bound is placed on the maximum possible size of a crack or flaw that might be present. The test method is specialized for the spherical balls that may have small spherical volumes for identifying a minimum size flaw.

Figure 3A:
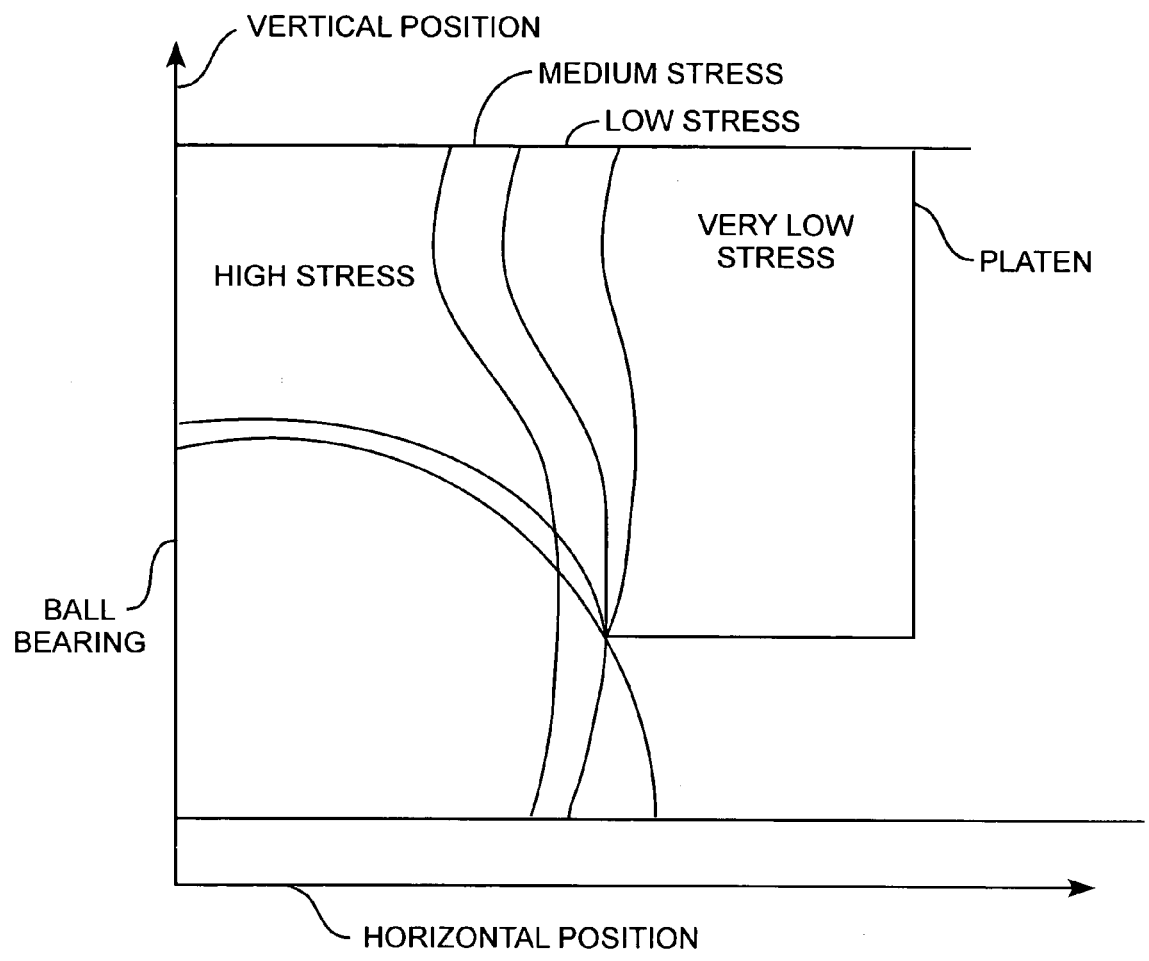
FIG. 3A is a compressive stress contour plot of a brittle ball under test.
Figure 3B:
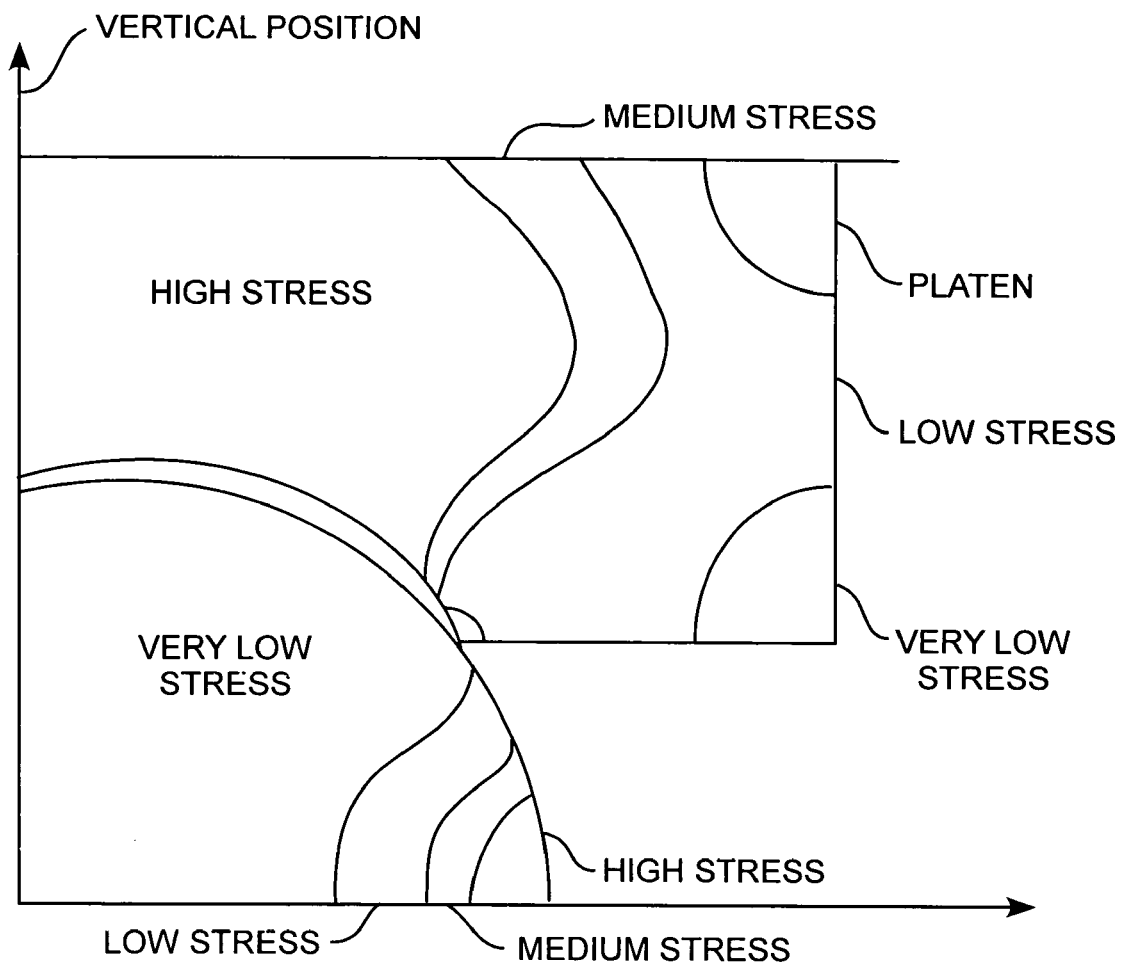
FIG. 3B is a tensile stress contour plot of a brittle ball under test.

Referring to FIGS. 1, 2, 3A, and 3B, and particularly FIGS. 3A and 3B, compressive stresses and tensile stresses are created in the ball under test, as well the top platen. Of particular interest is the hoop tensile stress that develops at the equator when the ball is compressed at the two poles. The tensile stress can be calculated using finite element analysis. An axisymmetric calculation can be performed to show the compressive and tensile stresses in a slice through the ball under test. The gradation from high, medium, low, and very low compressive stress and tensile stress extends through the ball and platen. The tensile stresses are highest at the equator. The compressive applied load is effectively translated into hoop tensile stress at the equator of the ball under test.

Figure 4:
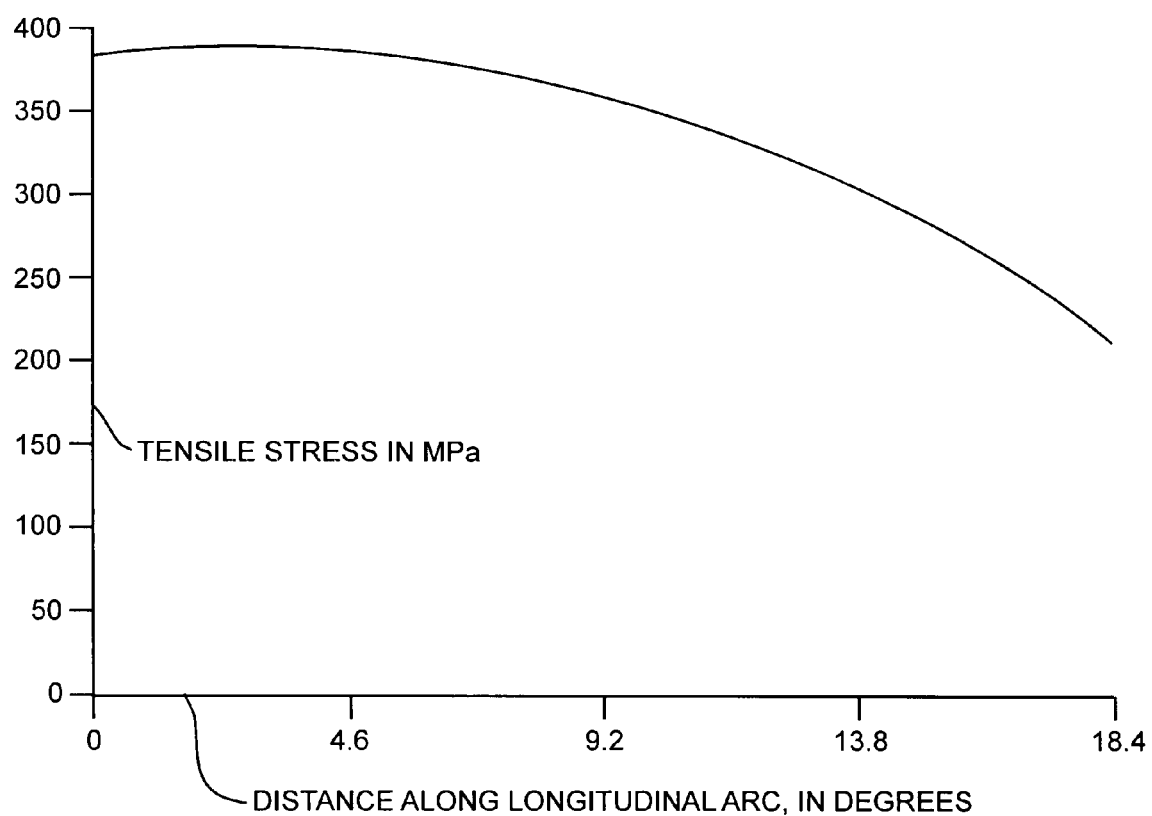
FIG. 4 is a graph of tensile stress as a function of longitudinal position north and south of the equator for a load applied to the soundproof test fixture.

Referring to all of the Figures, and particularly to FIG. 4, the tensile stress is shown for a typical load applied to the test fixture as a function of the longitudinal position north and south of the equator. The position is measured in terms of degrees of longitude along the arc from the equator to the pole. As shown, the tensile stress is 300 MPa at a longitudinal position of 13.8° and is 350 MPa at a position of 9.2°. The half penny crack is characterized by the radius r. Consequently, a halfpenny crack has a length of 2r on the surface, and it is this surface length of 2r that is comparable to the crack length detected by conventional dye penetrant technique. The stress intensity factor K for the half penny crack is a function of r and the applied tensile stress σ and is given by the accepted simplified fracture toughness equation, $K=1.33\sigma\sqrt{\pi}\sqrt{r}$. In the fracture toughness equation, σ is the tensile stress, r is the radius of the flaw, and K is the fracture toughness. Hence, the r radial size of the flaw is related to the applied stress σ for a given fracture toughness K. The stress is, in turn, related to applied load by. A typical value for K for the silicon nitride balls is 5.0 MPa$\sqrt{m}$ from independent measurement. The simplified fracture toughness equation represents an accepted approximation that is valid under the assumption that the half penny crack is a perfect half circle, which is commonly observed. Using the example of a tensile stress of 300 MPa, the fracture toughness equation shows that a flaw whose radius is greater than or equal to 0.05 mm will grow. This flaw corresponds to a crack whose surface length is 0.1 mm. At a tensile stress of 350 MPa, the flaw radius is 0.04 mm, which corresponds to a crack with surface length of 0.08 mm.

The tensile stress σ is related to the applied load. A predetermined amount of stress causes a predetermined sized flaw to grow. The stress upon a flaw is a function of the applied load. Hence, for a given fracture toughness, the growth of the predetermined sized flaw is a function of load. When an acoustical sound is observed at a given load for a predetermined fracture toughness, the flaw size is determined. As the load increases, at some predetermined load, or stress, the flaws exceeding the maximum allowable flaw size will grow and emit sound. That is, the acoustical test method for a predetermined maximum allowable flaw, can be used by applying a load up to a predetermined stress level. If an acoustical sound is emitted, then there is a flaw exceeding the maximum allowable size. If no acoustical sound is emitted, there is no flaw exceeding the maximum allowable size. Hence, the test method can use different load level to screen lots of balls having maximum allowable flaws. The stress level and maximum allowable size flaws can be determined empirically, through lot testing.

If the predetermined maximum allowable flaw size is 0.1 mm, then a calculation shows that the portion of the ball within a longitudinal arc of 13.8° of the equator can be tested under the application of a typical load to the test fixture. Simply by turning the ball seven times through successive steps of 13.8° that the entire volume of the ball is swept through the equator, then the entire ball can be proof tested to this requirement. If the predetermined maximum allowable flaw size is 0.08 mm, then the ball simply has to be turned through fourteen steps of 9.2° to proof test the ball.

The invention is directed to an acoustical test method that directly monitors emissions from crack or flaw growth at an applied load for directly identifying balls have flaws exceeding a maximum allowable size. The method is precise and immune to errors. The ball under test is compressed along the north and south poles of the ball, which causes the equatorial bulging under high tensile stresses where crack growth occurs at a sufficiently high-applied load. The conforming mating hemispherical platens are incompletely conforming, that is less than 90° in arc length angle from the poles. Too low an angle and the ball is crushed at the poles. At too high an angle, the equator does not bulge to give required tensile hoop stress. Finite element analysis shows that an arc length angle α of 75°+/−10° is preferred. The acoustic test method identifies a maximum allowable flaw size in a wide variety of brittle material balls including ceramics and steel ball bearings, such as 52100 steel bearing class balls with fracture toughnesses K up to 15.0 MPa$\sqrt{m}$.

The test method enables direct identification of flaws exceeding a maximum allowable size in ball bearings, such as silicon-nitride balls used in hybrid bearings. The test can be applied using variously sized balls of differing materials and flaw sizes. Those skilled in the art can make enhancements, improvements, and modifications to the invention, and these enhancements, improvements, and modifications may nonetheless fall within the spirit and scope of the following claims.

What is claimed is:

1. A method for identifying a flaw exceeding a predetermined maximum allowable size in a ball having an equator, the equator defining north and south poles of the ball, the method comprising the steps of,
   applying an applied load in compression through opposing hemispherical surfaces having an arc length angle of less than ninety degrees, the opposing hemispherical surfaces conforming to the surfaces of the ball respectively at the north and south poles so that the ball bulges outwardly at the equator producing tensile stresses,
   determining a critical applied load when the flaw begins to grow and emit sound under the tensile stresses at the equator, and
   detecting acoustical emission at the applied load for identifying a flaw exceeding the predetermined maximum allowable flaw size.

2. The method of claim 1 wherein,
   the ball has a fracture toughness less than 15.0 MPa$\sqrt{m}$.

3. The method of claim 1 wherein,
   the arc length angle is 75°±10 °.

4. The method of claim 1 wherein,
   the ball is made of silicon nitride.

5. The method of claim 1 wherein,
   the ball is a made of a ceramic material.

6. The method of claim 1 wherein,
   the ball is made of steel.

7. The method of claim 1 wherein,
   the applied load creates an applied stress field as a maximum principal stress in MPa, and
   the maximum principal stress is related from the size and material of the ball.

8. The method of claim 1 wherein,
   the applied load is applied through a load frame applying the applied load to a top platen having a top conforming socket defining a top hemispherical surface of the opposing hemispherical surfaces, and
   the ball is disposed in a bottom platen having a bottom conforming socket defining a bottom hemispherical surface of the opposing hemispherical surfaces.

9. The method of claim 1 wherein the detecting step comprising,
   predetermining a predetermined applied load when the applied load causes a flaw having the maximum allowable size to grow,
   monitoring the flaw during the applying step, and
   terminating the applied load when the applied load reaches the predetermined applied load,
   detecting acoustical sounds emitted from the flaw during the applying step for determining that the flaw in the ball exceeds the maximum allowable flaw size.

10. The method of claim 1 wherein the monitoring step uses a microphone focused upon the equator of the ball during the applying step.

11. The method of claim 1 wherein,
    the applied load is applied through a load frame applying the applied load to a top platen having a top conforming socket defining a top hemispherical surface of the opposing hemispherical surfaces, and the ball is disposed in a bottom platen having a bottom conforming socket defining a bottom hemispherical surface of the opposing hemispherical surfaces, the method further comprising the steps of, rotating the ball within the top and bottom platens, and repeating the applying step and determining and detecting step.

12. The method of claim 11 further comprising the steps of, repeating the rotating and repeating steps a plurality of times for placing tensile stresses at respective angular positions of the ball for completely testing the ball for the flaws disposed anywhere within the ball.

* * * * *